US00PP33966P3

(12) United States Plant Patent
Beatson

(10) Patent No.: US PP33,966 P3
(45) Date of Patent: Feb. 22, 2022

(54) HOP PLANT NAMED 'NZH131'

(50) Latin Name: ***Humulus lupulus* L.**
Varietal Denomination: NZH131

(71) Applicant: New Zealand Hops Limited, Nelson (NZ)

(72) Inventor: Ron Beatson, Motueka (NZ)

(73) Assignee: New Zealand Hops Limited, Nelson (NZ)

( * ) Notice: Subject to any disclaimer, the term of this patent is extended or adjusted under 35 U.S.C. 154(b) by 0 days.

(21) Appl. No.: 17/300,155

(22) Filed: Mar. 31, 2021

(65) Prior Publication Data

US 2021/0315142 P1 Oct. 7, 2021

Related U.S. Application Data

(60) Provisional application No. 63/004,338, filed on Apr. 2, 2020.

(51) Int. Cl.
*A01H 6/28* (2018.01)
*A01H 6/00* (2018.01)
*A01H 5/02* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
CPC ..... A01H 6/28; A01H 5/02
See application file for complete search history.

*Primary Examiner* — Keith O. Robinson
(74) *Attorney, Agent, or Firm* — Leydig, Voit & Mayer, Ltd.

(57) ABSTRACT

A new and distinct hop plant is described. The new cultivar results out of selection from a population of seedlings derived from deliberate crossing 'Hersbrucker Pure' (seed parent; not patented) and tetraploid selection 00.L123-168 (pollen parent; not patented). The new cultivar, 'NZH131', is characterised by having cones which are mid-season maturing and having medium alpha acid content. The new cultivar is suitable for beer flavouring

4 Drawing Sheets

Genus and species of plant claimed: *Humulus lupulus* L.
Variety denomination: 'NZH131'.

BACKGROUND OF THE INVENTION

The new cultivar of hop, *Humulus lupulus* L., was created in the course of a planned breeding program carried out at Motueka, New Zealand. It was selected from a population of seedlings derived from crossing 'Hersbrucker Pure' (seed parent; not patented) and tetraploid selection 00.L123-168 (pollen parent; not patented). The cross was carried out in January 2012. Seedlings from the cross were grown in a nursery at the same location and subsequently planted in the field in November 2012. They remained in the field for 2 seasons (2012-13 and 2013-14) to allow for agronomic and chemistry traits to be measured and/or assessed. The genotype, 'NZH131', was identified as having potential as a new cultivar. During the 2014-15 season it was clonally propagated using soft tip methods at Motueka, New Zealand. The resulting plants were found to be true to type demonstrating that the characteristics of the new cultivar 'NZH131' are stable and transmitted without change through succeeding generations.

SUMMARY OF THE INVENTION

A new and distinct hop plant is described. The 'NZH131' cultivar is characterised by having cones which are mid-season maturing, and medium alpha acid content with high amounts of geraniol and significant amounts of citrus-piney compounds, The new cultivar is suitable for beer flavouring.

In 2014-15, 'NZH131' was clonally propagated using soft tip methods at Motueka, New Zealand. The resulting plants were found to be true to type demonstrating that the characteristics of the new cultivar 'NZH131' are stable and transmitted without change through succeeding generations.

In 2015 it was decided to advance 'NZH131' due to its agronomic and chemistry properties for further testing including brewing trials. Further plants were propagated and a trial plot was planted in 2017-18. Brewing trials were conducted in the 2017 to 2020 seasons.

'NZH131' is maintained at Motueka, New Zealand, where it has undergone observations for uniformity. All plants have been found to be true to type, that is, no off types have been observed. 'NZH131' is distinguished from its parent female parent, 'Hersbrucker Pure' as 'NZH131' has mid-season cone maturation while 'Hersbrucker Pure' has a very early cone maturation. 'NZH131' has long cones that are cylindrical in longitudinal cross section while 'Hersbrucker Pure' has medium length cones that are medium ovate in longitudinal cross section. The pollen parent, 00.L123-168, is a male and thus does not produce cones.

Under New Zealand growing conditions 'NZH131' is distinguished from varieties of common knowledge by the following characteristics: When compared to 'Wakatu™' (not patented) and 'Cascade' (not patented) 'NZH131' has cones that mature later. In addition, 'NZH131' has cones that are cylindrical in longitudinal cross section, while 'HORT3829' (patented; U.S. Plant Pat. No. 23,985), 'Wakatu™' and 'Dr Rudi' (not patented) have cones that are narrow ovate and 'Cascade' has cones that are medium ovate in longitudinal cross section. The density of the foilage of the side shoot from the middle third of the plant of 'NZH131' is dense while the foliage of 'HORT3829' and 'Cascade' is of sparse density and 'Wakatu™' is medium density. The main shoot of 'NZH131' has weak anthocyanin coloration while 'Wakatu™', 'Cascade' and 'Dr Rudi' have absent or very weak anthocyanin coloration. When compared to 'HORT3829', 'Wakatu™', 'Cascade' and 'Dr Rudi', which have an even distribution of laterals, 'NZH131' has a distribution of laterals predominately in the top third.

BRIEF DESCRIPTION OF THE DRAWINGS

The accompanying photographs show typical specimens of the plant habit, cones, and leaves of the new cultivar as depicted in colours as nearly true as is reasonably possible to make the same in colour illustration of this character. The plants shown in these photographs were six years old.

BOTANICAL DESCRIPTION

Figure 1:
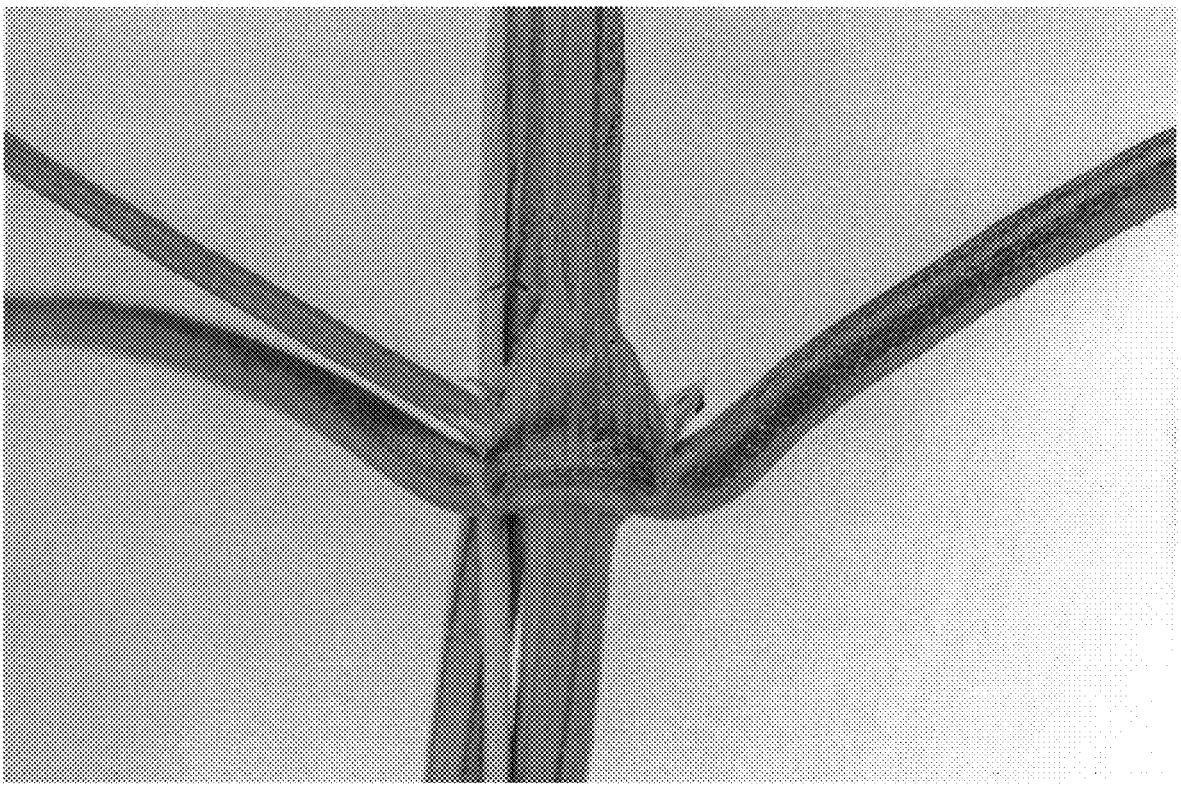
FIG. 1: 'NZH131' stipule.
Figure 2:
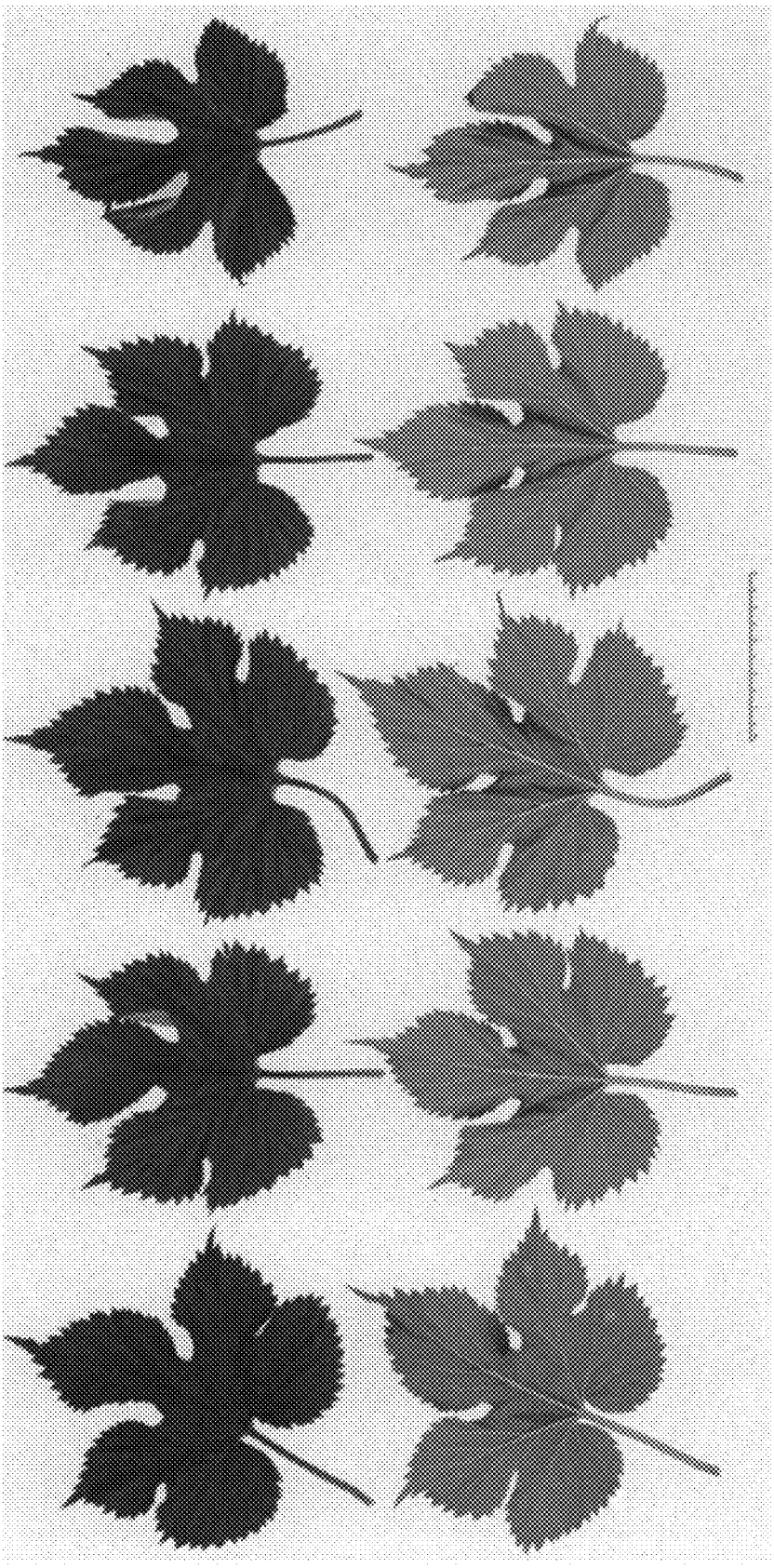
FIG. 2: 'NZH131' upper and under side of leaves.
Figure 3:
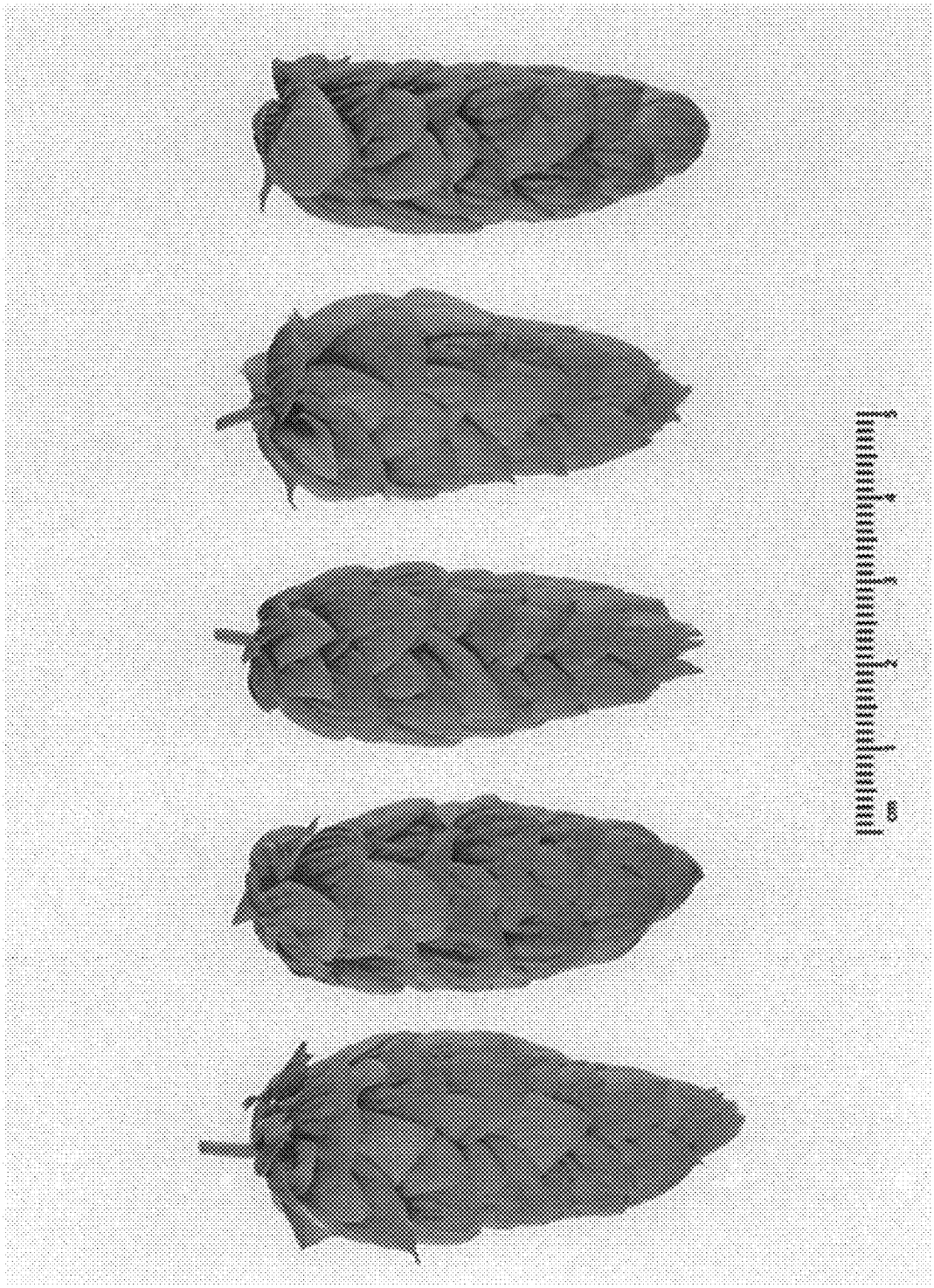
FIG. 3: 'NZH131' cones.
Figure 4:
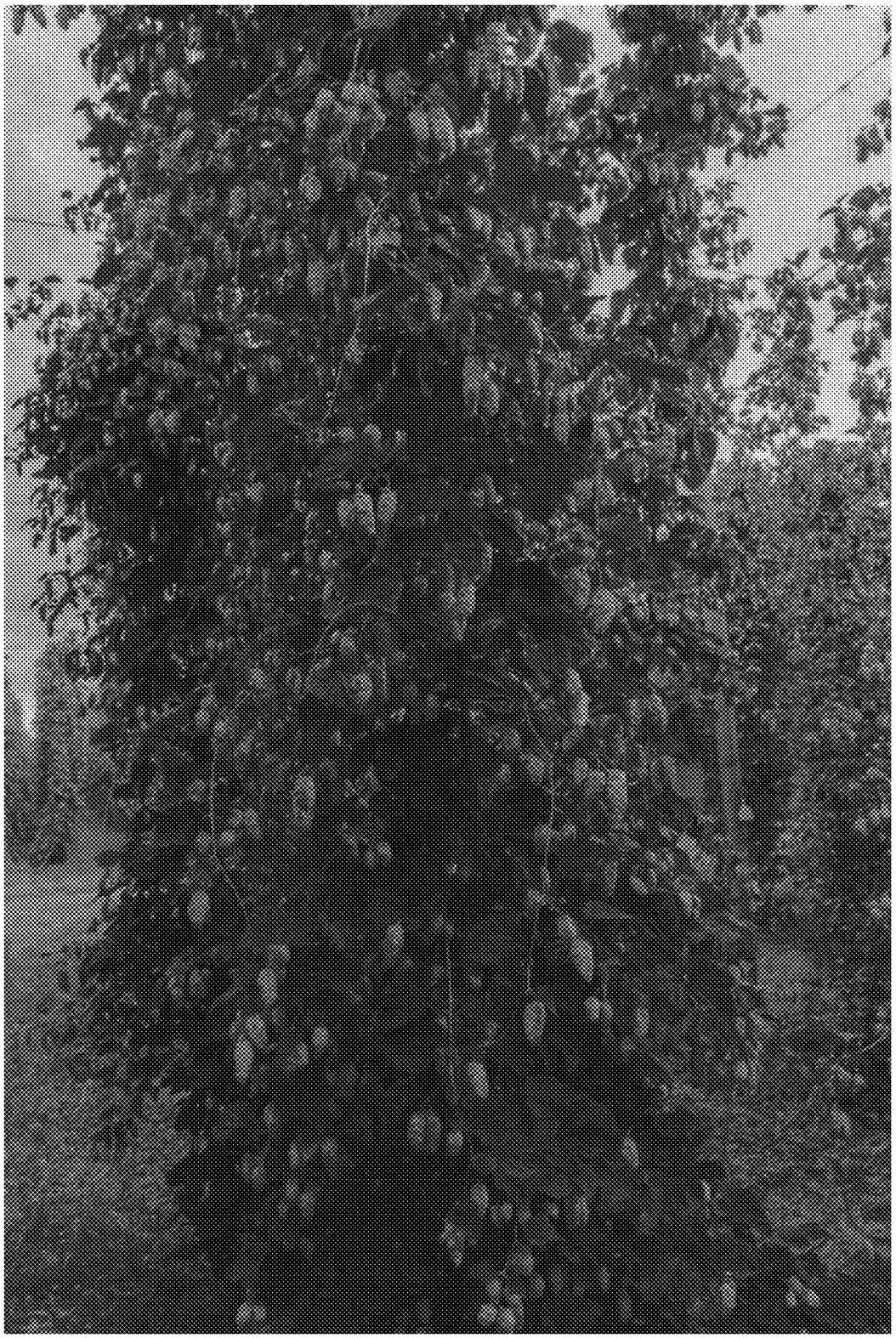
FIG. 4: 'NZH131' whole plant.

The following is a description of the new cultivar with colour terminology in accordance with The Royal Horticultural Society Colour Charts (R.H.S.C.C.) 2001 edition. The specimens described were six years old and were grown at Motueka, New Zealand. The observations were made over the 2019-2021 seasons.

Plant form and vigour: Mature plants had a normal growth type and produced a yield (averaging 2.21 tonnes/ha) of mid-season maturing cones. The shape of the plant tended to be cylindrical to club shaped with the head being high to very high volume. The main shoot of a one year old plant had an average vine diameter half way up the vine of 9.8 mm, and anthocyanin coloration was weak. Node pubescence was weak. The average internode length was 213 mm.

Laterals: The attitude of the laterals was spreading. The side shoots from the middle third of the plant were medium in length, averaged 52 cm, and produced a medium number of cones, an average of 2.5 per node. The side shoots from the top third of the plant had an average length of 60 cm and produced an average of 2 cones/node. There was an average of 8 nodes per lateral in the middle third of the plant and an average of 9.4 nodes per lateral in the upper third of the plant. Stipule pose is upright and stipule colour is green 144A.

Leaves: The leaves were lobed with predominantly three lobes. The large, weakly blistered leaves were opposite with crenate margins. The average leaf length was 176 mm and average width was 210 mm. The upper leaf surface colour was near, Green, 136A with medium intensity. Venation type is palmate and venation colour is 144A. Petioles have an average length of 93 mm, an average width of 5.5 mm and the colour is 30A.

Foliage density: The density of the foliage of the side shoot from the middle third of the plant for NZH131 was dense.

Cones: Were long and cylindrical in shape in longitudinal section; in cross section they were square in shape. The cone average length was 46.6 mm and average width 18.8 mm. Bracts were medium-large in size, with an average length of 20.5 mm and average width of 11.9 mm, Green in colour, 145C. The cones were slightly open and the bract apex was medium in length. Bracteole had an average length of 17 mm and average width of 9.6 mm. The bracterole colour was 157B. Strigs were medium length, and had an average length of 38.2 mm, with an average width of 3.3 mm. The colour of the strig was Green, 145B.

Physiological timing: Flowering commences mid-season in Motueka, New Zealand around the 5-15 January. Harvest is mid-season in the New Zealand season, commencing mid-March, under normal conditions.

Chemistry profile: 'NZH131' has undergone extensive chemistry profile testing. 'NZH131' has medium alpha acid levels around 9%, low Beta acid levels around 3% and cohumulone levels around 30%.

Use: Primarily flavouring and bittering ingredient for beer.

Pest and disease: 'NZH131' does not appear particularly resistant or susceptible to any particular pests or diseases known to afflict *Humulus lupulus*.

Hardiness: The plant cold hardiness according to the American zone classification has not been determined.

The invention claimed is:

1. A new and distinct hop plant named 'NZH131', substantially as illustrated and described herein.

* * * * *